US008729311B2

(12) United States Patent
Zhou et al.

(10) Patent No.: US 8,729,311 B2
(45) Date of Patent: May 20, 2014

(54) CATALYSTS FOR CONVERTING ACETIC ACID TO ACETONE

(75) Inventors: Zhenhua Zhou, Houston, TX (US); Radmila Jevtic, Pasadena, TX (US); Victor J. Johnston, Houston, TX (US); Heiko Weiner, Pasadena, TX (US)

(73) Assignee: Celanese International Corporaton, Dallas, TX (US)

( * ) Notice: Subject to any disclaimer, the term of this patent is extended or adjusted under 35 U.S.C. 154(b) by 167 days.

(21) Appl. No.: 13/371,078

(22) Filed: Feb. 10, 2012

(65) Prior Publication Data
US 2013/0210936 A1    Aug. 15, 2013

(51) Int. Cl.
*C07C 45/41* (2006.01)

(52) U.S. Cl.
USPC .......................................................... 568/391

(58) Field of Classification Search
USPC .......................................................... 568/397
See application file for complete search history.

(56) References Cited

U.S. PATENT DOCUMENTS

| 1,315,544 | A | 9/1919 | Curme, Jr. |
|---|---|---|---|
| 1,892,742 | A | 1/1933 | Walter et al. |
| 2,697,729 | A | 12/1954 | Ohlson et al. |
| 2,882,244 | A | 4/1959 | Milton |
| 3,130,007 | A | 4/1964 | Breck |
| 3,408,267 | A | 10/1968 | Miller et al. |
| 3,445,345 | A | 5/1969 | Katzen et al. |
| 3,466,334 | A | 9/1969 | Young et al. |
| 3,478,112 | A | 11/1969 | Karl et al. |
| 3,864,284 | A | 2/1975 | Clippinger et al. |
| 3,884,981 | A | 5/1975 | Kiff |
| 3,981,923 | A | 9/1976 | Stouthamer et al. |
| 3,990,952 | A | 11/1976 | Katzen et al. |
| 4,275,228 | A | 6/1981 | Gruffaz et al. |
| 4,306,942 | A | 12/1981 | Brush et al. |
| 4,310,712 | A | 1/1982 | Langley |
| 4,319,058 | A | 3/1982 | Kulprathipanja et al. |
| 4,352,940 | A | 10/1982 | Adelman et al. |
| 4,398,039 | A | 8/1983 | Pesa et al. |
| 4,454,358 | A | 6/1984 | Kummer et al. |
| 4,456,775 | A | 6/1984 | Travers et al. |
| 4,465,854 | A | 8/1984 | Pond et al. |
| 4,471,136 | A | 9/1984 | Larkins et al. |
| 4,480,115 | A | 10/1984 | McGinnis |
| 4,492,808 | A | 1/1985 | Hagen et al. |
| 4,497,967 | A | 2/1985 | Wan |
| 4,514,515 | A | 4/1985 | Travers et al. |
| 4,626,321 | A | 12/1986 | Grethlein et al. |
| 4,628,130 | A | 12/1986 | Bournonville et al. |
| 4,678,543 | A | 7/1987 | Houben et al. |
| 4,692,218 | A | 9/1987 | Houben et al. |
| 4,754,074 | A | 6/1988 | Hussmann |
| 4,842,693 | A | 6/1989 | Wheldon |
| 4,886,905 | A | 12/1989 | Larkins et al. |
| 4,961,826 | A | 10/1990 | Grethlein et al. |
| 4,985,572 | A | 1/1991 | Kitson et al. |
| 4,990,655 | A | 2/1991 | Kitson et al. |
| 4,994,608 | A | 2/1991 | Torrence et al. |
| 5,001,259 | A | 3/1991 | Smith et al. |
| 5,015,786 | A | 5/1991 | Araki et al. |
| 5,026,908 | A | 6/1991 | Smith et al. |
| 5,035,776 | A | 7/1991 | Knapp |
| 5,103,066 | A | 4/1992 | Dessau |
| 5,124,004 | A | 6/1992 | Grethlein et al. |
| 5,144,068 | A | 9/1992 | Smith et al. |
| 5,149,680 | A | 9/1992 | Kitson et al. |
| 5,185,481 | A | 2/1993 | Muto et al. |
| 5,198,592 | A | 3/1993 | Van Beijnum et al. |
| 5,250,271 | A | 10/1993 | Horizoe et al. |
| 5,414,161 | A | 5/1995 | Uhm et al. |
| 5,426,246 | A | 6/1995 | Nagahara et al. |
| 5,449,440 | A | 9/1995 | Rescalli et al. |
| 5,502,248 | A | 3/1996 | Funk et al. |
| RE35,377 | E | 11/1996 | Steinberg et al. |
| 5,599,976 | A | 2/1997 | Scates et al. |
| 5,770,770 | A | 6/1998 | Kim et al. |
| 5,821,111 | A | 10/1998 | Grady et al. |
| 5,861,530 | A | 1/1999 | Atkins et al. |
| 5,942,460 | A | 8/1999 | Garland et al. |
| 5,973,193 | A | 10/1999 | Crane et al. |
| 6,040,474 | A | 3/2000 | Jobson et al. |
| 6,093,845 | A | 7/2000 | Van Acker et al. |
| 6,143,930 | A | 11/2000 | Singh et al. |

(Continued)

FOREIGN PATENT DOCUMENTS

| EP | 0104197 | 4/1984 |
|---|---|---|
| EP | 0167300 | 1/1986 |

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

(Continued)

*Primary Examiner* — Sikarl Witherspoon

(57) ABSTRACT

The present invention relates to a process for the formation of acetone from acetic acid. The process is conducted at an elevated temperature of above 225° C. by contacting a feed stream containing acetic acid, and an optional carrier gas, with a catalyst. The catalyst comprises a support that is favorable for the production of acetone. The support may comprise titania, zirconia, ceria, silica, iron oxide, and carbon, but preferably is titania, zirconia, and ceria.

20 Claims, No Drawings

(56) References Cited

U.S. PATENT DOCUMENTS

| | | |
|---|---|---|
| 6,232,352 B1 | 5/2001 | Vidalin et al. |
| 6,265,618 B1 | 7/2001 | Zoeller et al. |
| 6,472,555 B2 | 10/2002 | Choudary et al. |
| 6,509,180 B1 | 1/2003 | Verser et al. |
| 6,525,230 B2 | 2/2003 | Grosso |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,765,110 B2 | 7/2004 | Warner et al. |
| 6,768,021 B2 | 7/2004 | Horan et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 6,933,414 B1 | 8/2005 | Stauffer |
| 7,005,541 B2 | 2/2006 | Cheung et al. |
| 7,074,603 B2 | 7/2006 | Verser et al. |
| 7,109,385 B2 | 9/2006 | Tatake et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,361,794 B2 | 4/2008 | Grosso |
| 7,375,049 B2 | 5/2008 | Hayes et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,816,565 B2 * | 10/2010 | Johnston et al. ............... 568/484 |
| 7,863,489 B2 | 1/2011 | Johnston et al. |
| 7,884,253 B2 | 2/2011 | Stites et al. |
| 7,888,082 B2 | 2/2011 | Verser et al. |
| 8,071,821 B2 | 12/2011 | Johnston et al. |
| 2002/0156328 A1 | 10/2002 | Grosso |
| 2003/0013908 A1 | 1/2003 | Horan et al. |
| 2003/0125589 A1 | 7/2003 | Grosso |
| 2004/0232049 A1 | 11/2004 | Dath et al. |
| 2004/0267074 A1 | 12/2004 | Grosso et al. |
| 2006/0019360 A1 | 1/2006 | Verser et al. |
| 2006/0127999 A1 | 6/2006 | Verser et al. |
| 2007/0106246 A1 | 5/2007 | Modesitt |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2008/0257784 A1 | 10/2008 | Dath et al. |
| 2009/0005588 A1 | 1/2009 | Hassan et al. |
| 2009/0023192 A1 | 1/2009 | Verser et al. |
| 2009/0069609 A1 | 3/2009 | Kharas et al. |
| 2009/0281354 A1 | 11/2009 | Mariansky et al. |
| 2010/0029980 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0249479 A1 | 9/2010 | Berg-Slot et al. |
| 2010/0273229 A1 | 10/2010 | Verser et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0185628 A1 | 8/2011 | Johnston et al. |
| 2011/0275861 A1 | 11/2011 | Johnston et al. |

FOREIGN PATENT DOCUMENTS

| | | |
|---|---|---|
| EP | 0400904 | 5/1990 |
| EP | 0372847 | 6/1990 |
| EP | 0456647 | 11/1991 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 823514 | 11/1959 |
| WO | WO 83/03409 | 10/1983 |
| WO | WO 2009/009320 | 1/2009 |
| WO | WO 2009/063174 | 5/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |

OTHER PUBLICATIONS

Claus, et al., "Selective Hydrogenolysis of Methyl and Ethyl Acetate in the Gas Phase on Copper and Supported Group VIII Metal Catalysts", Applied Catalysis A, 79, 1991, pp. 1-18.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

* cited by examiner

CATALYSTS FOR CONVERTING ACETIC ACID TO ACETONE

FIELD OF THE INVENTION

The present invention relates to catalysts for converting acetic acid to acetone, to processes for making such catalysts, and to processes for reducing acetic acid using the catalyst.

BACKGROUND OF THE INVENTION

Although numerous industrial processes have been used to manufacture acetone, conventionally acetone is obtained as a co-product of phenol production by the Hock Process. In this process, benzene is alkylated in the presence of a Friedel-Crafts catalyst with propylene to produce cumene, which in turn is oxidized to cumene hydroperoxide (CHP). CHP is then hydrolyzed in an acidic medium to yield phenol and acetone. There are several variations of the Hock Process. For example, U.S. Pat. No. 5,015,786 describes the preparation of cumene by alkylating an aromatic compound, the preparation of phenol via cumene, and the alkylation of an aromatic compound using an alcohol as the alkylating agent. U.S. Pat. No. 4,310,712 describes a process where CHP is decomposed to phenol and acetone by mixing it with acetone and a catalyst. U.S. Pat. No. 7,109,385 describes a process for producing a phenol product generally comprising the first step of reacting CHP and water with an acid catalyst to produce the phenol product, and the second step of passing the phenol product through a second reactor to decompose the residual CHP.

When there is a demand imbalance between phenol and acetone, however, the co-production using the Hock Process is not efficient or economic.

Other industrial process for producing acetone include dehydrogenation of 2-propanol, as described in GB823514. Propylene is absorbed in concentrated sulfuric acid to produce isopropyl sulfate, which is then hydrolyzed to 2-propanol. The 2-propanol is then oxidized to produce acetone. U.S. Pat. No. 3,981,923 describes alumina-supported platinum or rhodium catalysts used for dehydrogenating lower secondary alcohols to ketones. U.S. Pat. No. 5,103,066 describes the catalytic dehydrogenation of alcohols to produce ketones and/or aldehydes using catalyst that comprises a platinum group metal and a non-acidic microporous crystalline support.

Each of these industrial processes are dependent on propylene. Since propylene is produced from natural gas liquids or refinery streams, its price has shown considerable volatility. This instability has impacted the economics of acetone manufacture. In addition, impurities in propylene often form unwanted by-products. Propylene is manufactured generally using crude oil as the starting material. Crude oil, however, contains sulfur compounds and various heavy metals, and these impurities are sometimes carried in propylene as trace contaminants during its manufacturing process. For example, carbonyl sulfide (COS) as a sulfur compound or arsenic as a heavy metal contaminant in propylene act as a catalyst poison in cumene preparation, thus disturbing normal progress of the cumene synthesis. Therefore, a strict purification process is needed to avoid contamination. Types and quantity of these contaminants, however, vary depending on not only the crude oil source but also the difference in the process conditions for the preparation of propylene from crude oil. Such irregularity burdens the propylene purification process with exceptionally complex and severe steps. Furthermore, conventional processes employ hazardous compounds such as concentrated sulfuric acid and benzene, a volatile carcinogen.

Alternatively, acetone may be produced by reacting formaldehyde with methyl chloride to produce acetone and hydrogen chloride. Methyl chloride is a toxic gas however, and formaldehyde is a known carcinogen. U.S. Pat. No. 6,933,414 describes a method for producing acetone via the reaction of formaldehyde with methyl chloride.

Various catalysts for converting acetic acid to acetone have been proposed. U.S. Pat. No. 1,892,742 describes a ketonization catalyst for converting acetic acid, acetylene, acetaldehyde, and ethyl acetate to acetone. The catalyst is porous charcoal containing oxides of iron, calcium, zinc, cerium, and thorium. U.S. Pat. No. 1,315,544 describes converting acetic acid to acetone using a catalyst comprising metallic iron in fine shavings. U.S. Pat. No. 2,697,729 describes a liquid phase pyrolysis of carboxylic acid and esters thereof to acetone using an activated alumina catalyst. U.S. Pat. No. 3,446,334 describes a process of converting aldehyde and acid to ketone using a catalyst containing lithium oxide on activated alumina. U.S. Pat. No. 4,754,074 describes converting carboxylic acids to aliphatic dialkyl ketone using a manganese dioxide on alumina catalyst. U.S. Pat. No. 6,265,618 discloses a process for the preparation of ketones, in particular cyclopropyl ketones, by contacting one or more carboxylic acids with a niobium catalyst at elevated temperatures. US Pub. No. 2011/0185628 described a ketonization reaction using a thorium oxide that converts acetic acid to acetone.

Therefore, it is an object of the present invention is to minimize the disadvantages of existing commercial processes for the production of acetone. One object of the present invention is to free producers from their dependence on propylene. Another object of the present invention is to provide a process in which acetone is the primary product. These and other objects, features, and advantages will be apparent from the following description.

SUMMARY OF THE INVENTION

In a first embodiment, the invention is directed to a process for producing acetone from acetic acid comprising contacting a feed stream containing acetic acid, and an optional carrier gas, at a an elevated temperature above 225° C. with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, ceria, and silica.

In a second embodiment, the invention is directed to a process for producing acetone from acetic acid comprising contacting a feed stream containing acetic acid, and an optional carrier gas, at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, and ceria, provided that when the support is titania the one or more metal is not rhenium.

In a third embodiment, the invention is directed to a process for producing acetone from acetic acid comprising contacting a feed stream containing acetic acid, and an optional carrier gas, at an elevated temperature with a catalyst comprising one or more metals selected from the group consisting of palladium and ruthenium on a silica support.

In a fourth embodiment, the invention is directed to a process for producing acetone from acetic acid comprising contacting a feed stream containing acetic acid, and an optional carrier gas, at an elevated temperature with a catalyst comprising one or more metals selected from the group consisting of copper and ruthenium on an iron oxide support.

In a fifth embodiment, the invention is directed to a process for producing acetone from acetic acid comprising contacting a feed stream containing acetic acid, and an optional carrier gas, at an elevated temperature with a catalyst comprising one or more metals selected from the group consisting of palladium and iron on a carbon support.

In a sixth embodiment, the invention is directed to a process for producing acetone from a carbonaceous material, comprising converting the carbonaceous feedstock to acetic acid, and contacting a feed stream containing the acetic acid and hydrogen at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, ceria, and silica.

In a seventh embodiment, the invention is directed to a process for producing acetone from a carbonaceous material, comprising converting the carbonaceous material into a first stream comprising syngas, converting at least some of said syngas into a second stream comprising methanol, separating some of said syngas into hydrogen and carbon monoxide, converting at least some of said methanol with some of said carbon monoxide into a third stream comprising acetic acid, and contacting a feed stream containing the acetic acid and hydrogen at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, ceria, and silica.

DETAILED DESCRIPTION OF THE INVENTION

In general this invention relates to a catalyst for converting acetic acid to acetone. In particular, the catalyst comprises a support that favors acetone production by reacting acetic acid at a high temperature. Advantageously, the present invention provides an industrially feasible route to acetone that does not use propylene and avoids aromatics.

Catalyst

In preferred embodiments, the catalyst comprises one or more metals selected from the group consisting of silver, gold, cobalt, chromium, copper, iron, iridium, nickel, palladium, platinum, rhenium, rhodium, ruthenium, and zinc. Copper, gold, palladium, or ruthenium are the most preferred active metals. Although two active metals may be used, it is generally preferably to use one active metal in the catalyst of the present invention. In some embodiments, copper may be combined with chromium or zinc. In one embodiment, copper and zinc may be used in substantially equal molar ratios, e.g., from 1.2:1 to 1:1.2 or about 1:1.

The metal loading may vary depending on the type of active metal. In general, the metal loading may vary from 0.5 to 25 wt. %, and more preferably from 1 to 20 wt. %. When copper, cobalt, iron, chromium or zinc are used the metal loading may be higher, e.g., from 3 to 25 wt. % or from 5 to 20 wt. %. Metal loadings around 20 wt. % may be suitable for copper, cobalt, iron, chromium, zinc, or combinations thereof. When silver, gold, iridium, nickel, palladium, platinum, rhenium, and ruthenium are used, lower metal loadings may be preferred. In one embodiment, the metal loading for silver, gold, iridium, nickel, palladium, platinum, rhenium, rhodium, and ruthenium may be from 0.5 to 2 wt. %, e.g., from 0.7 to 1.5 wt. %, or about 1 wt. %. Lower individual metal loadings may be used when combination of metals are used provided that the total metal loading of all metals is less than 25 wt. %.

For producing acetone, the type of support strongly influences the conversion of acetic acid and selectivity to acetone. The support may be selected from the group consisting of titania, zirconia, ceria, silica, iron oxide, and carbon. In one embodiment, support may be selected from the group consisting of titania, zirconia, ceria, and silica. In one embodiment, the support is present in an amount from 75 wt. % to 99.5 wt. %, e.g., from 80 wt. % to 99 wt. %. Although each of these supports may favor acetone production, depending on the active metal, at high temperatures, titania, zirconia, and ceria are the most preferred supports.

In some embodiments the support may also comprise a support modifier. In one embodiment, the total weight of the support modifiers may be present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Support modifiers may adjust the acidity of the support. For example, the acid sites, e.g. Brønsted acid sites, on the support may be adjusted by the support modifier to favor selectivity to acetone during the hydrogenation of acetic acid. The acidity of the support may be adjusted by reducing the number or reducing the availability of Brønsted acid sites on the support. The support may also be adjusted by having the support modifier change the pKa of the support. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of modified supports that adjusts the acidity of the support to make the support less acidic or more basic favors formation of acetone over other products.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $Nb_2O_5$, $MnO_2$, $CuO$, $Co_2O_3$, and $Bi_2O_3$.

In some embodiments, particular combinations of supports and active metals may favor acetone production. In one embodiment, when silica is used as the support, the most preferred active metals are palladium and ruthenium. In another embodiment, when iron oxide is used as the support, the most preferred active metals are copper and ruthenium. In another embodiment, when carbon is used as the support, the most preferred active metals are palladium and iron. In some embodiments, particular combinations of supports and active metals may not favor acetone production and thus are not preferred. For example, when titania is the support it is preferred not to use rhenium in the catalyst.

Exemplary catalysts for producing acetone including the following. A first catalyst may comprise copper in an amount of about 20 wt. % on titania. A second catalyst may comprise copper and zinc, in substantially equal molar ratios, having a total metal loading of about 20 wt. % on titania. A third catalyst may comprise palladium in an amount of about 20 wt. % on titania. A fourth catalyst may comprise palladium in an amount of about 1 wt. % on zirconia. A fifth catalyst may comprise ruthenium in an amount of about 1 wt. % on zirconia. A sixth catalyst may comprise gold in an amount of about 1 wt. % on ceria. Other various combinations of the metals and preferred supports may also produce acetone by hydrogenating acetic acid.

Process to Make Catalyst

The present invention also relates to processes for making the catalyst. One or more support modifiers, if desired, may also be added to the support by mixing or through impregnation. Powdered materials of the modified supports or a precursor thereto may pelletized, crushed and sieved and added to the support. The use of a solvent, such as water, glacial acetic acid, a strong acid such as hydrochloric acid, nitric acid, or sulfuric acid, or an organic solvent, may be preferred. The resulting mixture may be stirred and added to additional support using, for example, incipient wetness techniques in which the precursor to the support modifier is added to a support having the same pore volume as the volume of the solution. Capillary action then draws the precursor to the support modifier into the pores in the support. The support containing precursor to the support modifier can then be formed by drying to drive off water and any volatile components within the support solution and depositing the tin on the support. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours.

Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support into desired size distribution can be employed.

In a preferred method of preparing the catalyst, the one or more metals are impregnated onto the support. A precursor of the one or more metals preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. When two metals are uses, multiple impregnation steps may be used.

Impregnation occurs by adding, optionally drop wise, either or both the metal precursor, preferably in suspension or solution, to the dry support. The resulting mixture may then be heated, e.g., optionally under vacuum, in order to remove the solvent. Additional drying and calcining may be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the two or more metals onto the support may occur simultaneously (co-impregnation) or sequentially. In simultaneous impregnation, the metal precursors are mixed together and added to the support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the two or more metal precursors in the event the two precursors are incompatible with the desired solvent, e.g., water.

In sequential impregnation, one of the metal precursors is first added to the support followed by drying and calcining, and the resulting material is then impregnated with the other metal precursor followed by an additional drying and calcining step to form the final catalyst composition.

Suitable metal precursors include, for example, metal halides, amine solubilized metal hydroxides, metal nitrates or metal oxalates. Generally, both from the point of view of economics and environmental aspects, aqueous solutions of soluble compounds are preferred. Calcining of the solution with the support and active metal may occur, for example, at a temperature of from 250° C. to 800° C., e.g., from 300° C. to 700° C. or about 500° C., optionally for a period of from 1 to 12 hours, e.g., from 2 to 10 hours, from 4 to 8 hours or about 6 hours.

Alkanoic Acid to Ketone

In one embodiment there is a process for producing acetone by reducing an alkanoic acid, and more preferable acetic acid, in the presence of the catalyst. The raw materials, acetic acid and/or a carrier gas, fed to the primary reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference.

The carrier gas may be selected from the group consisting of hydrogen, nitrogen, argon, helium, carbon dioxide or combinations thereof. Preferably, the carrier gas is hydrogen. Although the carrier gas may be inert, in some embodiment such as when hydrogen is used, the hydrogen may also reduce the acetic acid. The carrier gas may be derived in whole or in part from syngas.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, when hydrogen is the carrier gas, the hydrogen may be supplied from syngas.

In some embodiments, some or all of the raw materials for the above-described acetic acid process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. The syngas, in turn, may be derived from variety of carbon sources. The carbon source, for example, may be selected from the group consisting of natural gas, oil, petroleum, coal, biomass, and combinations thereof. Syngas may also be obtained from bio-derived methane gas, such as bio-derived methane gas produced by landfills or agricultural waste.

In another embodiment, the acetic acid used in the reaction may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen carrier gas that may be used in the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used as the carrier gas in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the reactor without the need for condensing the acetic acid and light ends or removing water, saving overall processing costs.

The acetic acid may be vaporized at the reaction temperature, following which the vaporized acetic acid may be fed along with the carrier gas. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with the carrier gas before vaporizing, followed by heating the mixed vapors up to the reactor inlet temperature. Preferably, the acetic acid is transferred to the vapor state by passing carrier gas through the acetic acid at a temperature at or below 150° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the catalysts may be used in conjunction with an inert material to regulate the pressure drop of the reactant stream through the catalyst bed and the contact time of the reactant compounds with the catalyst particles.

The reaction in the reactor may be carried out in either the liquid phase or vapor phase. Preferably, the reaction is carried out in the vapor phase at elevated temperatures under the following conditions. The reaction temperature may be at least 225° C., e.g. at least 235° C. or at least 325° C. In terms of ranges, the reaction temperature may range from 225° C. to 425° C., e.g., from 235° C. to 425° C., from 245° C. to 400° C. The pressure may range from 10 kPa to 3000 kPa, e.g., from 50 kPa to 2500 kPa, from 100 kPa to 2250 kPa, or from 200 kPa to 2100 kPa. The reactants may be fed to the reactor at a gas hourly space velocity (GHSV) greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The reaction optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

The molar ratio of carrier gas to acetic acid in the feed stream may vary from 100:1 to 1:100, e.g., from 50:1 to 1:50, or from 20:1 to 1:20.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, the reaction of acetic acid may achieve favorable conversion of acetic acid and favorable selectivity and productivity to acetone. For purposes of the present invention, the term "conversion" refers to the amount of acetic acid in the feed that is converted to a compound other than acetic acid. Conversion is expressed as a percentage based on acetic acid in the feed. The conversion of acetic acid may be at least 10%, e.g., at least 20%, at least 40%, at least 50%, at least 60%, at least 70% or at least 80%. Although catalysts that have high conversions are desirable, especially acetic acid conversions that are at least 80% or at least 90%, in some embodiments a low acetic acid conversion may be acceptable at high selectivity for acetone. It is, of course, well understood that in many cases, it is possible to compensate for low acetic acid conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to acetone, we refer to the acetone selectivity as 60%. Preferably, the catalyst have a selectivity to acetone is at least 60%, e.g., at least 70%, or at least 80%. Preferably, the selectivity to acetone may be high and is at least 75%, e.g., at least 80% or at least 85%. The selectivity to other compounds, such as acetaldehyde, ethanol, and/or ethyl acetate is preferably less than the selectivity to acetone.

Preferred embodiments of the process also have low selectivity to undesirable products, such as methane, ethane, and carbon dioxide. Carbon dioxide may be a byproduct of this process. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., acetone, formed during the hydrogenation based on the kilograms of catalyst used per hour. A productivity of at least 100 grams of acetone per kilogram of catalyst per hour, e.g., at least 400 grams of acetone per kilogram of catalyst per hour or at least 600 grams of acetone per kilogram of catalyst per hour, is preferred. In terms of ranges, the productivity preferably is from 100 to 3,000 grams of acetone per kilogram of catalyst per hour, e.g., from 400 to 2,500 grams of acetone per kilogram of catalyst per hour or from 600 to 2,000 grams of acetone per kilogram of catalyst per hour.

The majority of acetone produced may be used as a precursor or intermediate to make other products such as methyl methacrylate, and methyl isobutyl alcohol. Methyl methacrylate is a monomer for PMMA which is used for making Plexiglas (acrylic glass). Methyl isobutyl alcohol is used to make methyl isobutyl ketone (MIBK) which is a common developer in lithography processes for semiconductor electronics. In addition, acetone is commonly used as a solvent or in products such as lacquers for automotive/furniture finishes, cellulose acetate films, degreasing/degumming agents, coatings/inks, resin thinners, general purpose cements, paint/varnish strippers, nail polish removers, and various cosmetic products. A summary of various uses for acetone is provided in Sifniades, S., Levy, A. B. and Bahl, H. 2011. Acetone. Ullmann's Encyclopedia of Industrial Chemistry, the entirety of which is hereby incorporated by reference.

For purposes of the present invention, acetone produced from acetic acid is substantially free from bis-phenol A.

The following examples describe the procedures used for the preparation of various catalysts employed in the process of this invention.

EXAMPLES

Example A

Cu/Zn on $TiO_2$ 1 g of titania (Degussa P25) of uniform particle size distribution was dried at 120° C. in an oven under nitrogen atmosphere overnight and then cooled to room temperature. Stock solutions of 0.5 $g_{salt}$/mL, of $Cu(NO_3)_2.3H_2O$ (Alfa Aesar) and 0.5 $g_{salt}$/mL, of $Zn(NO_3)_3.6H_2O$ (Alfa Aesar) were prepared in water. A mixture of 457.6 μL of the stock copper solution, 564.3 μL of the stock zinc solution and 188.1 μL of water was prepared and this mixture was impregnated on 1 g of the support. The impregnation was repeated so that the total active metal loading was 20 wt. %. Cu and Zn were added in equal molar amounts. The impregnated catalyst was dried at 50° C. in air with a ramp rate of 1° C./minute, followed by a ramp rate of 2° C./minute up to 120° C. The catalyst was kept at 120° C. for 2 hours and then calcined at 450° C. for four hours with a 2° C./minute heating rate in air.

Example B

Cu on $TiO_2$ 1 g of titania (Degussa P25) of uniform particle size distribution was dried at 120° C. in an oven under nitrogen atmosphere overnight and then cooled to room temperature. A stock solution of 0.5 $g_{salt}$/mL, of $Cu(NO_3)_2.3H_2O$ (Alfa Aesar) was prepared in water. A mixture of 929.5 μL of the stock copper solution and 280.5 μL of water was prepared and this mixture was impregnated on 1 g of the support. The impregnation was repeated so that the total active metal loading of copper was 20 wt. %. The drying and calcining of Example A was repeated for this catalyst material.

Example C

Comparative—Cu/Zn on $SiO_2$—$Al_2O_3$

Silica-alumina (1 g) of uniform particle size distribution was dried at 120° C. in an oven under nitrogen atmosphere overnight and then cooled to room temperature. The support contained 13.4 wt. % $Al_2O_3$. A mixture of 457.6 μL of the stock copper solution from Example A, 564.3 μL of the stock zinc solution from Example A and 518.1 μL of water was prepared and this mixture was impregnated on 1 g of the silica-alumina support. The impregnation was repeated so that the total active metal loading of copper and zinc was 20 wt. %. The drying and calcining of Example A was repeated for this catalyst material.

Example D

Comparative—Cu on $SiO_2$—$Al_2O_3$

Silica-alumina (1 g) of uniform particle size distribution was dried at 120° C. in an oven under nitrogen atmosphere overnight and then cooled to room temperature. 929.5 μL of the stock copper solution from Example B and 610.5 μL of water was prepared and this mixture was impregnated on 1 g of the silica-alumina support. The impregnation was repeated so that the total active metal loading of copper was 20 wt. %. The drying and calcining of Example A was repeated for this catalyst material.

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify: Acetaldehyde, Ethanol, Acetone, Methyl acetate, Vinyl acetate, Ethyl acetate, Acetic acid, Ethylene glycol diacetate, Ethylene glycol, Ethylidene diacetate, and Paraldehyde. The middle channel was equipped with a TCD and Porabond Q column and was used to quantify: $CO_2$, Ethylene, and Ethane. The back channel was equipped with a TCD and Porabond Q column and was used to quantify: Helium, Hydrogen, Nitrogen, Methane, and Carbon monoxide.

An acetic acid feed liquid was evaporated and charged to the reactor along with hydrogen and helium as carrier gases with an average combined gas hourly space velocity (GHSV) of about 2430 $hr^{-1}$ at a temperature of about 250° C. and pressure of 2500 kPa. A portion of the vapor effluent was passed through a gas chromatograph for analysis of the contents of the effluents. The conversion of acetic acid and selectivities are reported in Table 1 at 20 and 60 TOS (time on stream—in hours).

TABLE 1

| | HOAc conversion (%) | | Selectivity (%) | | | | | |
|---|---|---|---|---|---|---|---|---|
| | | | Acetone | | EtOAc | | AcH | |
| | | | TOS | | | | | |
| | 20 | 60 | 20 | 60 | 20 | 60 | 20 | 60 |
| Ex. A | 19 | 19 | 82 | 82 | 0 | 0 | 3 | 3 |
| Ex. B | 25 | 30 | 85 | 85 | 0 | 0 | 0 | 0 |
| Ex. C | 20 | 15 | 10 | 15 | 65 | 65 | 3 | 2 |
| Ex. D | 55 | 23 | 0 | 1 | 70 | 87 | 0 | 1 |

As shown in Table 1, catalysts from Examples A and B were more favorable for producing acetone over comparative catalysts from Examples C, and D.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the above descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing acetone from acetic acid comprising: contacting a feed stream containing acetic acid at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, and ceria; wherein the acetic acid conversion is greater than 10% and further wherein the acetic acid selectivity to acetone is greater than 60%.

2. The process of claim 1, wherein the elevated temperature is above 225° C.

3. The process of claim 1, wherein the elevated temperature is from 225° C. to 425° C.

4. The process of claim 1, wherein the elevated temperature is from 235° C. to 425° C.

5. The process of claim 1, wherein the catalyst comprises from 0.5 to 25 wt. % of the one or more metals.

6. The process of claim 1, wherein the catalyst comprises from 1 to 20 wt. % of the one or more metals.

7. The process of claim 1, wherein the catalyst comprises a substantially equal molar ratio of copper and zinc.

8. The process of claim 1, wherein the acetic acid conversion is greater than 20%.

9. The process of claim 1, wherein the acetic acid selectivity to acetone is greater than 80%.

10. The process of claim 1, wherein when the support is titania the one or more metals is not rhenium.

11. The process of claim 1, further comprising gasifying a carbonaceous material to produce the feed stream, wherein the carbonaceous material is selected from the group consisting of oil, coal, natural gas and biomass.

12. The process of claim 1, wherein the feed stream further comprises a carrier gas.

13. The process of claim 12, wherein the carrier gas is selected from the group consisting of hydrogen, nitrogen, argon, helium, carbon dioxide and combinations thereof.

14. A process for producing acetone from acetic acid comprising: contacting a feed stream containing acetic acid at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, and ceria, provided that when the support is titania the one or more metals is not rhenium; wherein the acetic acid selectivity to acetone is greater than 60%.

15. A process for producing acetone from acetic acid comprising: contacting a feed stream containing acetic acid at an elevated temperature with a catalyst comprising one or more metals selected from the group consisting of palladium and ruthenium on a silica support; wherein the acetic acid selectivity to acetone is greater than 60%.

16. A process for producing acetone from acetic acid comprising: contacting a feed stream containing acetic acid at an elevated temperature with a catalyst comprising one or more metals selected from the group consisting of copper and ruthenium on an iron oxide support; wherein the acetic acid selectivity to acetone is greater than 60%.

17. A process for producing acetone from acetic acid comprising: contacting a feed stream containing acetic acid at an elevated temperature with a catalyst comprising one or more metals selected from the group consisting of palladium and iron on a carbon support; wherein the acetic acid selectivity to acetone is greater than 60%.

18. A process for producing acetone from a carbonaceous material, comprising:
   converting the carbonaceous material to acetic acid; and
   contacting a feed stream containing the acetic acid at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, ceria, and silica; wherein when the support is silica, the catalyst comprises palladium and ruthenium and further wherein the acetic acid selectivity to acetone is greater than 60%.

19. A process for producing acetone from a carbonaceous material, comprising:
   converting the carbonaceous material into a first stream comprising syngas;
   converting at least some of said syngas into a second stream comprising methanol;
   separating some of said syngas into hydrogen and carbon monoxide;
   converting at least some of said methanol with some of said carbon monoxide into a third stream comprising acetic acid; and
   contacting a feed stream containing the acetic acid and hydrogen at an elevated temperature with a catalyst comprising one or more metals selected from the group consisting of silver, gold, cobalt, chromium, copper, iron, iridium, nickel, palladium, platinum, rhenium, rhodium, ruthenium, and zinc on a support selected from the group consisting of titania, zirconia, and ceria, wherein the acetic acid selectivity to acetone is greater than 60%.

20. The process of claim 19, wherein the carbonaceous material is selected from the group consisting of oil, coal, natural gas and biomass.

* * * * *